(12) United States Patent
Cai et al.

(10) Patent No.: US 11,864,769 B2
(45) Date of Patent: Jan. 9, 2024

(54) COMPLETELY LAPAROSCOPIC STAGED HEPATECTOMY USING ROUND-THE-LIVER LIGATION AND ITS INSTRUMENT

(71) Applicant: ZHEJIANG UNIVERSITY, Hangzhou (CN)

(72) Inventors: Xiujun Cai, Hangzhou (CN); Shuyou Peng, Hangzhou (CN); Yifan Wang, Hangzhou (CN); Chen Lu, Hangzhou (CN); Mingyu Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 154 days.

(21) Appl. No.: 17/470,808

(22) Filed: Sep. 9, 2021

(65) Prior Publication Data
US 2022/0361887 A1 Nov. 17, 2022

(30) Foreign Application Priority Data
May 14, 2021 (CN) .......................... 202110529657.7

(51) Int. Cl.
*A61B 17/12* (2006.01)
*A61B 17/128* (2006.01)
(Continued)

(52) U.S. Cl.
CPC .... *A61B 17/12013* (2013.01); *A61B 17/1285* (2013.01); *A61B 17/1325* (2013.01);
(Continued)

(58) Field of Classification Search
CPC ........ A61B 17/12009; A61B 17/12013; A61B 17/1285; A61B 17/1322; A61B 17/1325;
(Continued)

(56) References Cited

U.S. PATENT DOCUMENTS 3,667,471 A * 6/1972 Doty ...................... A61B 17/12
24/280
3,991,444 A * 11/1976 Bailey ................ B65D 63/1063
24/16 PB (Continued)

*Primary Examiner* — Ryan J. Severson
(74) *Attorney, Agent, or Firm* — Muncy, Geissler, Olds & Lowe, P.C.

(57) ABSTRACT

A laparoscopic staged hepatectomy using round-the-liver ligation is carried out includes: (1) a laparoscopic operation is performed with general anesthesia using round-the-liver ligation, the branches of the portal vein of the hemiliver are ligated, a tourniquet is used to tighten the connecting part between the right and left hemilivers to block the communicating blood flow between the hemiliver to be removed and the hemiliver to be reserved, a drainage tube is put into the peritoneal cavity, then close the peritoneal cavity; (2) the patient gradually resumes eating after the first operation, and recuperate to make the volume of the hemiliver increase to an expected volume; (3) after the hemiliver increases to the expected volume, a laparoscopic liver resection is carried out with general anesthesia to remove the diseased hemiliver, and then the patient is nursed to be completely recovered. An instrument for implementing the laparoscopic staged hepatectomy is also disclosed.

3 Claims, 6 Drawing Sheets

(51) Int. Cl.
*A61B 17/132* (2006.01)
*A61B 17/00* (2006.01)

(52) U.S. Cl.
CPC .............. *A61B 17/1327* (2013.01); *A61B 2017/00407* (2013.01); *A61B 2017/12004* (2013.01)

(58) Field of Classification Search
CPC ...... A61B 17/1327; A61B 2017/00407; A61B 2017/12004
See application file for complete search history.

(56) References Cited

U.S. PATENT DOCUMENTS

| | | | | |
|---|---|---|---|---|
| 4,730,615 | A * | 3/1988 | Sutherland | A61B 17/823 24/30.5 P |
| 5,203,786 | A * | 4/1993 | Vernick | A61B 17/12 24/274 WB |
| 5,304,188 | A * | 4/1994 | Marogil | A61B 17/12009 606/157 |
| 5,314,437 | A * | 5/1994 | Holtsch | A61B 17/1327 606/151 |
| 5,549,619 | A * | 8/1996 | Peters | A61B 17/064 606/151 |
| 9,023,066 | B2 * | 5/2015 | Pasricha | A61B 17/12013 606/232 |
| 9,757,131 | B2 * | 9/2017 | Sanders | A61B 17/085 |
| 10,399,755 | B2 * | 9/2019 | Sanders | B65D 63/02 |
| 11,337,704 | B2 * | 5/2022 | Kaneda | A61B 17/12009 |
| 11,364,032 | B2 * | 6/2022 | Cabrera Aquino | A61B 17/12013 |
| 2005/0261708 | A1 * | 11/2005 | Pasricha | A61B 17/0401 606/139 |
| 2006/0253128 | A1 * | 11/2006 | Sekine | A61B 17/32056 606/139 |
| 2009/0149876 | A1 * | 6/2009 | Patel | A61B 17/32056 606/151 |
| 2010/0234862 | A1 * | 9/2010 | Patel | A61B 17/12009 606/151 |
| 2016/0361063 | A1 * | 12/2016 | Sanders | A61B 17/085 |
| 2017/0240327 | A1 * | 8/2017 | Sanders | B65D 63/18 |
| 2018/0161041 | A1 * | 6/2018 | Cai | A61B 17/1322 |
| 2021/0161534 | A1 * | 6/2021 | Kaneda | A61B 17/12009 |
| 2022/0361887 | A1 * | 11/2022 | Cai | A61B 17/1327 |

* cited by examiner

COMPLETELY LAPAROSCOPIC STAGED HEPATECTOMY USING ROUND-THE-LIVER LIGATION AND ITS INSTRUMENT

TECHNICAL FIELD

The invention relates to a liver resection, especially to a completely laparoscopic staged hepatectomyusing round-the-liver ligation for patients with severe liver cirrhosis or liver tumor.

BACKGROUND OF THE INVENTION

China is the country which has spent the most social cost for hepatitis B, liver cirrhosis and liver cancer in the world. The hepatitis B, liver cirrhosis and liver cancer are closely associated with hepatitis B virus infectionand reflect different stages of disease development after being infected with hepatitis B virus,and many patients infected with hepatitis B virus can finally develop liver cancer.The public data shows that among the 350 million carriers with hepatitis B globally, nearly 100 million are Chinese people, and among the 0.7 million deaths associated with viral hepatitis globally, half of the deaths are Chinese people. Primary liver cancer is a common malignant tumor in China and is in the second place of death rate among the malignant tumors. Although liver resection is the most effective therapy for patients with liver cancer, not all of the patients can toleratethe liver resection. A majority of the patients with liver cancer has had hepatitis B for decades, are concomitant with liver cirrhosis, have poor compensative capacity and can't undergo major hepatectomy, which gives rise to a high risk of postoperative hepatic failure and even death. The size of the future liver remnant (FLR) is a limiting factor of how extensive liver resection can be carried out in a patient. In general, the FLR should be at least 40% for liver cancer patients with a compromised liver cirrhosis. The patients whose FLR can't meet the requirement have to abandon the liver resection and wait for liver transplantation. However, liver transplantation is facing a shortage of donors, so a majority of the patients can not have the liver transplantation.

In recent years, associating liver partition and portal vein ligation for staged hepatectomy (ALPPS) gradually receives the attention of hepatobiliary surgery. The technology adopting two operations is used for performing liver resection on patients who were considered to be incapable of undergoing liver resection before. In the first stage operation, the branches of the portal vein of the hemiliver to be removed is cut off, the left hemiliver and right hemiliver are cut off and separated, and after the operation, the volume of the hemiliver to be reserved will increase rapidly. Then the second stage operation is performed to remove the diseased hemiliver. From the current experience, the technology can be used for carrying out liver resection on liver cancer patients who could not undergo liver resection before, and achieves good treatment effect. The existing method can: (1) reduce bleeding in the operation; (2) reduce ischemia reperfusion injury; (3) allow anatomical liver resection to be performed, protect the function of the reserved hemiliver; and (4) reduce dissemination of tumor. However, some problems exist in the technology, wherein the most important one is that the first operation needs to cut off and separate the left and right hemilivers to block the communicating blood flow between the left and right hemilivers, and the risk of bile leakage from the transection of liver parenchyma is great. In Regensburg hospital in German, the occurrence rate of bile leakage in the operation is up to 24%. In addition, if the interval time between the two operations is too long, excessive adhesion in the peritoneal cavity can be easily generated; if the interval time is too short, due to large wound surface area, patients have to undergo the second operation before they recover enough.

SUMMARY OF THE INVENTION

The invention aims to overcome the above-mentioned defects in the prior art, and provide a two-step liver resection and its instument capable of preventing bile leakage from the transection of liver parenchyma, which allows a patient to undergo the first stage operation and the second stage operation under complete laparoscope, so that the operation wound surface is greatly reduced, and postoperative recovery and liver regeneration are facilitated.

According to the invention, the completely laparoscopic staged hepatectomy using round-the-liver ligation adopts the technical scheme as follows:

the completely laparoscopic staged hepatectomy using round-the-liver ligation is characterized in thatit is completed through two operations with the interval time of 6 to 15 days, and the steps are as below:

(1) The first operation: a complete laparoscopic operation is performed with general anesthesia using round-the-liver ligation, the branches of the portal vein of the hemiliver to be removed are ligated, meanwhile a tourniquet is used to tighten the connecting part between the right and the left hemilivers to block the communicating blood flow between the hemiliver to be removed and the hemiliver to be reserved, a drainage tube is put into the peritoneal cavity at the hepatic hilus, then close the peritoneal cavity, and the operation is completed;

(2) Short-term liver nourishing: the patient gradually resumes eating after the first operation, and recuperate for 6-15 days to make the volume of the hemiliver to be reserved increase to the expected volume of the future liver remnant, in which the expected volume of the future liver remnant should be at least 30-40% of the standard liver volume, and the standard liver volume (SLV)=706.2×BSA+ 2.4, wherein BSA=$BW^{0.425} \times BH^{0.725} \times 0.007184$, in which BW represents body weight(kg), BH represents body height (cm), BSA represents body surface area($m^2$), and SLV represents standard liver volume (ml);

(3) The second operation: after the volume of the hemiliver to be reserved has increased to the expected volume of the future liver remnant, a complete laparoscopic liver resection is carried out with general anesthesia to remove the diseased hemiliver, and then the patient is nursed to be completely recovered.

Generally, when the patient is a patient with liver cirrhosis, preferably, the expected volume of the future liver remnant is at least 40% of standard liver volume; when the patient is a patient without liver cirrhosis, preferably the expected volume of the future liver remnant is at least 30% of standard liver volume.

The invention uses the round-the-liver tourniquet to tighten the connecting part between the right and the left hemilivers to block the communicating blood flow between the right and the left hemilivers.

The step (1) of the present invention is recommended to be performed as follows: under laparoscope, separate the parahepatic ligaments from the liver, dissect the first porta hepatis, separate the hepatic artery and the portal vein of the diseased hemiliver, expose the superior heptic vein fossa between the right hepatic vein and the main trunk of the middle and left hepatic veins at the second porta hepatis, separate the post-hepatic inferior vena cava, ligate part of the short hepatic vein, expose the inferior right hepatic vein, ligate and cut off the veins of the hemiliver to be removed, protect the veins of the hemiliver to be reserved, then use a round-the-liver tourniquet to block the communicating blood flow between the hemiliver to be removed and the hemiliver to be reserved, put a drainage tube into the peritoneal cavity at the hepatic hilus, and then close the peritoneal cavity.

Preferably, a locking ring capable of adjusting the tightness of the round-the-liver tourniquet is arranged at the enclosing position of the round-the-liver tourniquet.

The locking ring is an elastic ring which is tightly matched with the periphery of the enclosed round-the-liver tourniquet. It is recommended that the locking ring is an elastic ring which is tightly matched with the closing of the round-the-liver tourniquet, and the elastic ring is tightly locked under the condition that the round-the-liver tourniquet keeps still, so that the round-the-liver tourniquet can be fixed and bound around the liver, and the binding on the liver can be tightened or loosened by lifting or loosening the round-the-liver tourniquet. Due to the fact that the elastic ring has high elasticity, the binding length of the round-the-liver tourniquet around the liver can be fixed at any time.

Further, for the first laparoscopic operation, the intersection of the left costal margin and the left clavicular line is served as the main manipulation port, after separating intraperitoneal adhesion, two accessory ports are taken at the right abdomen.

More further, the second operation is performed with the same ports as those of the first laparoscopic oprreation.

If the hemiliver to be removed is the left hemiliver, the first operation in step (1) is preferably performed as follows: the intersection of the left costal margin and the left clavicular line is served as the main manipulation port, after separating intraperitoneal adhesion with ultrasonic dissector, take two accessory ports at the right abdomen, separate intraperitoneal adhesion and the adhesion at the hepatic hilus and the second porta hepatis, dissect the proper hepatic artery, the left hepatic artery and the left portal vein, the root of the left portal vein is ligated with silk thread and then occluded with a Hamlock, the left hepatic artery is marked with Proline, and the treatment of the first porta hepatis is completed, then, cut off the coronary ligament and the left triangular ligament, separate the left hemiliver; dissect the left hepatic vein at the second porta hepatis, pass a wire-assisted nasogastric tube through the right side of the left hepatic vein, attach the nasogastric tube tightly to the surface of the liver, and move it around to the front of the left caudate lobe, after the left hepatic artery, move the tube around to the front of the liver, near the root of the left hepatic pedicle; then, put the two ends of the round-the-liver tube together, pull them out of the body through a port in the abdominal wall positioned at the right clavicular line, the wire-assisted nasogastric tube is put in a 36F chest tube, tightened as the round-the-liver tourniquet and clamped by a hemal forceps after being pushed into the outer sleeve, intraoperative ultrasonography is used to determine the diseased part of the liver before tightening the round-the-liver tourniquet, a drainage tube is put into the peritoneal cavity at the hepatic hilus, and then close the peritoneal cavity.

Similarly, if the hemiliver to be removed is the right hemiliver, the first operation can be performed by referring to the above-mentioned operational steps.

Furthermore, if the hemiliver to be removed is the left hemiliver, the second operation is preferably performed according to following steps: enter the peritoneum through the same port as that in the first laparoscopic operation, use an aspirator for cleaning the effusion and pushing and plucking the adhesions to expose the hepatic hilus, then lift the round-the-liver tourniquet through the abdominal wall, find the marked left hepatic artery at the hepatic hilus, occlude and cut off the left hepatic artery, later use laparoscopic Peng's multifunctional operative dissector (LPMOD) to transect the liver parenchyma around the round-the-liver tourniquet by curettage and aspiration, which is assisted with anEndo-GIA stapler, transect the liver parenchyma after the left hepatic vein is clipped, remove the diseased hemiliver, completely check for bleeding sites in the peritoneal cavity, and retain a peritoneal drainage tube at the transection of liver parenchyma and close the peritoneal cavity.

Similarly, if the hemiliver to be removed is the right hemiliver, the second operation can be performed by referring to the above-mentioned operational steps.

Specifically, in step (2), the patient after first operation gradually resumes eating, and on the 6th day after the first operation, the round-the-liver tourniquet should be tightened downwards once more.

In step (3), preferably, the second operation should be performed after the volume of the hemiliver to be reserved has increased to at least 60% of the standard liver volume within 6-15 days after the first operation. If the interval time is too short, the volume of the future live remnantmay be too small;otherwise, if the interval time is too long, excessive adhesion in the peritoneal cavity can be easily generated. So that the interval time is preferably 1-2 weeks, and is usually not recommended to exceed 2 weeks.

The invention adopts a completely laparoscopic staged hepatectomy using round-the-liver ligation. The first-stage operation is performed to ligate the branches of the portal vein of the hemiliver to be removed under complete laparoscopic operation, the connecting part between the left liver and the right liver is also tightened to block the communicating blood flow between the left and right liver. After the operation, size of the hemiliver to be reserved will rapidly increase.

Then, the second-stage operation is performed to remove the diseased hemiliver. The method adopts a laparoscopic technology. In this way, the operation wound surface is greatly reduced, so that the impact on the immune system of the organism and the influence on the anti-tumor capacity of the body are reduced, the early rehabilitation of the patient can be achieved, and the patient can accept other anti-tumor auxiliary treatment earlier. The technology uses the round-the-liver tourniquet to replace parenchymal transection to block the communicating blood flow between the left and right liver, so that the complication of bile leakage from the transection of liver parenchymais thoroughly prevented. The operation cost is 30% of the cost of the conventional liver transplantation, so the economic burden of the patient's family can be reduced.

The invention also includes a special instrument for implementing the completely laparoscopic staged hepatectomy using round-the-liver ligation, and it is a pressure-adjustable liver tightening device.

Although there is a precedent for using elastic loops to tighten the liver, the prior art still has the following shortcomings: First, the tightening force of the band around the liver is completely dependent on the experience of the doctor during installation, and it is not easy to grasp, and it is easy to be too loose or too loose. To be too loose will not completely block the communication of blood flow of the left and right livers, and will not achieve the purpose of surgery. To be too tight will damage the liver tissue; second, because the interval between the first and second stage of operations is as long as 6-15 days, the atrophy of the joint between the livers is large, even with the elastic ring, the tightness of the band around the liver changes greatly, and it cannot always be maintained at the optimal level, which affects the realization of the purpose of surgery; third, the band around the liver is located Inside the human body, the degree of tightness is difficult to be recognized by the doctor, which affects the doctor to adjust the hepatic band in time; fourth, the adjustment of the tightness of the hepatic band after the first-stage operation depends on the doctor's personal experience and hand feeling, which cannot be accurately measured, and the blindness is relatively large. Therefore, in order to reduce the difficulty of implementing the surgical method of the present invention, it is necessary to improve its surgical instruments.

A special instrument for implementing the completely laparoscopic staged hepatectomy using round-the-liver ligation, a pressure-adjustable liver tightening device, including a liver-around band 5 made of flexible materials of which one end is a free end, and the other end is provided with a through hole. The free end passes through the through hole to form a loop that can tighten the liver 4; the side of the liver-around band 5 facing away from the liver is defined as the outside; The outer side of the liver-around band 5 is provided with first ratchet teeth 51; the free end of the liver-around band 5 passes through the through hole, the abdominal wall catheter 6, and the pressure control device 7 in sequence, and the abdominal wall catheter 6 passes through the patient's abdominal wall 2.

The pressure control device 7 includes a first sleeve 72 and a buckle 71. The direction of the central axis of the first sleeve 72 is taken as the longitudinal direction. The first sleeve 72 is provided with a longitudinal first inner hole 721 for passing through the liver-around band 5, and the buckle 71 is fixed in the longitudinal guide groove 722 of the first sleeve 72 and can move longitudinally along the guide groove 722; the buckle 71 is provided with a second ratchet tooth 711 extending into the first inner hole 721; When the liver-around band 5 passing through the first sleeve 72, the first ratchet tooth 51 meshes with the second ratchet tooth 711; the second ratchet tooth 711 allows the first ratchet tooth 51 to slide in the positive direction of tightening the loop while preventing the first ratchet tooth 51 from sliding in the reverse direction.

A spring 73 arranged in the longitudinal direction is installed between the buckle 71 and the first sleeve 72.

The buckle 71 is provided with a vernier 714 for marking the tightness of the liver-around band 5, and a scale 723 of the vernier 714 is provided on the first sleeve 72.

Preferably, the buckle 71 is a second sleeve sleeved in the first sleeve 72 which is provided with a longitudinal second inner hole 712 for passing the liver-around band 5; The outer wall of the second sleeve is provided with a protruding portion 713 which is slidably inserted in the longitudinal guide groove 722 on the first sleeve 72, and the aforementioned vernier 714 is provided on the protruding portion 713, and the inner wall of the second sleeve is provided with the second ratchet tooth 711.

Preferably, the other end of the liver-around band 5 opposite to the free end is provided with a base 52, and the through hole is provided on the base 52; under the pulling force of the liver-around band 5, the first sleeve 72 and the abdominal wall catheter 6 and the base 52 press in sequence to position the liver-around band 5.

The first sleeve 72, the buckle 71 and the spring 73 of the present invention are configured to set physical parameters in accordance with the requirements for the tightening force of the liver during the operation. In the first stage of surgery, when the tightness of the liver-around band reaches the preset value, the vernier on the buckle is aligned with the scale of the first sleeve, and the surgeon can fix the position of the liver-around band, thus the rely on the personal experience of the physician can be avoided.

Between the first stage and second stage of surgery, the connecting part connecting the left and right liver lobes shrinks, and the tension of the liver-around band drops. The vernier and scale on the pressure control device 7 can directly reflect this change. Since the pressure control device 7 is located outside the body, the doctor can conveniently observe the changes of the tightness of the liver-around band 5 and make adjustments without opening the abdomen. Therefore, the doctor can conveniently keep the tightening force of the liver-around band 5 on the liver at an optimal value at any time.

Compared with traditional methods, the improved laparoscopic two-step liver resection has the following beneficial effects: (1) the present invention uses the round-the-liver tourniquet to replace parenchymal transection to block the-communicating blood flow between the left and right livers, so that the complication of bile leakage from the transection of liver parenchymais thoroughly prevented. Meanwhile, the two operations are both performed under laparoscope, the operation wound surface is greatly reduced, so that the impact on the immune system of the organism and the influence on the anti-tumor capacity of the body are reduced.Besides, early rehabilitation of the patient can be achieved, and the patient can accept other anti-tumor auxiliary treatment earlier. (2)The present invention use the round-the-liver ligation under complete laparoscope. This invention allows the patients with liver cirrhosis or liver cancer but cannot tolerate the liver resection to undergo staged liver resection, in which tumors are thoroughly removed. The problem that the liver cancer patients concomitant with liver cirrhosis cannot be subjected to the liver resection due to the fact that the volume of the future liver remnant is less than 40% is solved, so that these patients can be effectively treated. It is worth mentioning that the operation is a good news for the patients who suffer from severe liver cirrhosis and need to do a major hepatectomy. In this way, the problem that the major hepatectomy cannot be carried out is solved, and the patient can undergo the operation without waiting for a liver donation. It is also a good news from an economic perspective, that the operation cost is 30% of the cost of the conventional liver transplantation, and the economic burden of the patient's family can be reduced. (3) The present invention overcomes the bile leakage from the transection of liver parenchyma in conventional staged hepatectomy. It solves the problem that the liver cancer patients concomitant with liver cirrhosis cannot be subjected to the liver resection due to the fact that the volume of the future liver remnant is less than 40% of the standard liver volume. After this surgery, patients have a good postoperative recovery, and the cost of treatment is reduced. (4) In the present invention, a locking ring (an elastic ring) is arranged at the enclosing position of the round-the-liver tourniquet. It can facilitate lifting and tightening the round-the-liver tourniquet during the operation, and tighten the closing of the round-the-liver tourniquet up at proper time.

In the first-stage operation, the instrument scale can be used to determine the degree of tightness of the liver-around band to avoid relying on the physician's personal experience; the doctor can directly observe the tightness of the band around the liver outside the patient's body, and easily adjust the tightness of the liver-around band to the liver and avoid opening the abdomen.

BRIEF DESCRIPTION OF THE DRAWINGS

In FIG. 4, (a) white arrow shows left portal vein, zebra arrow shows left hepatic artery; (b) white arrow, left hepatic vein; (c) intraoperative ultrasound determines the tumor is at the left side of the round-the-liver tourniquet and detects the flow of communicating branch before tightening the round-the-liver tourniquet; (d) the abdominal incision condition after the first operation, white arrow shows the external part of the tourniquet, which is occluded by a hemal forceps.

In FIG. 5, (a) ulcerationon the surface of the left liver and adhesion; (b) marked left artery; (c) LPMOD, curettage and aspiration; (d) white arrow shows left portal vein, and zebra arrow shows left hepatic artery.

DETAILED DESCRIPTION OF THE PREFERRED EMBODIMENT

Figure 1:
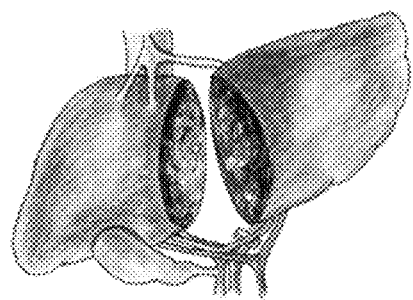
FIG. 1 is a schematic figure of Traditional ALPPS (transection of liver parenchyma).

The following description is used to disclose the present invention so that those skilled in the art can implement the present invention. The preferred embodiments in the following description are only examples, and those skilled in the art can think of other obvious variations. The basic principles of the present invention defined in the following description can be applied to other embodiments, modifications, improvements, equivalents, and other technical solutions that do not deviate from the spirit and scope of the present invention.

Those skilled in the art should understand that, in the disclosure of the present invention, the terms "longitudinal", "lateral", "upper", "lower", "front", "rear", "left", "right", and the orientation or positional relationship indicated by "vertical", "horizontal", "top", "bottom", "inner", "outer", etc. are based on the orientation or positional relationship shown in the drawings, which is only for the convenience of describing the present invention and the description is simplified, rather than indicating or implying that the device or element referred to must have a specific orientation, be constructed and operated in a specific orientation, and therefore the above-mentioned terms should not be construed as limiting the present invention.

In the present invention, the term "a" in the claims and specification should be understood as "one or more", that is, in one embodiment, the number of an element may be one, and in another embodiment, the number of the element It can be multiple. Unless it is clearly stated in the disclosure of the present invention that the number of the element is only one, the term "one" cannot be understood as unique or singular, and the term "one" cannot be understood as a limitation on the number.

In the description of the present invention, it should be understood that "first", "second", etc. are only used for descriptive purposes, and cannot be understood as indicating or implying relative importance. In the description of the present invention, it should be noted that unless otherwise clearly specified and limited, the terms "connected" and "linked" should be understood in a broad sense. For example, it may be a fixed connection, a detachable connection or an integral connection. It can be a mechanical connection or an electrical connection; it can be a direct connection or an indirect connection through a medium. For those of ordinary skill in the art, the specific meaning of the above-mentioned terms in the present invention can be understood according to specific circumstances.

In the description of this specification, descriptions with reference to the terms "one embodiment", "some embodiments", "examples", "specific examples", or "some examples" etc. mean specific features described in conjunction with the embodiment or example. , Structure, materials or features are included in at least one embodiment or example of the present invention. In this specification, the schematic representations of the above terms do not necessarily refer to the same embodiment or example. Moreover, the described specific features, structures, materials or characteristics can be combined in any one or more embodiments or examples in a suitable manner. In addition, those skilled in the art can combine and combine the different embodiments or examples and the features of the different embodiments or examples described in this specification without contradicting each other.

EXAMPLE 1

1. Clinical data

A 61-year-old female was admitted to the hospital due to elevated AFP for 5 days. Past medical history showd that she had chronic HBV for almost 30 years, and been treated by the antiviral drugs of Lamivudine and Adefovir dipivoxil. She underwent an open operation of right liver nodule resection plus cholecystectomy 2 years before, after which the pathological findings showed liver cirrhosis (crude nodule) and chronic atrophic cholecystitis. Physical examination revealed a bronze-colored face, the height of 156 cm and the weight of 47 kg but no liver palms, spider nevus and jaudice. Abdominal examination revealed no tenderness and rebound tenderness. Related lab exams showed elevated AFP of 39.94 μg/L. The liver function was accessed to be class A according to Child-Pugh score. Upper abdominal enhancement CT showed occupied lesions in liver segment II (first consider the liver cancer), cirrhosis, splenomegaly, absence of the gallbladder and slightly dilated intrahepatic bile duct (see FIG. 1a). MRCP showed mild left hepatic bile duct dilation and the absence of gallbladder. Then she underwent percutaneous liver biopsy, and the pathology showed well-differentiated hepatocellular carcinoma (left liver tissue). She was prepared to take left hepatectomy. The standard liver volume (SLV) was calculated to be 1010 mL(SLV=706.2×BSA×2.4, BSA=$BW^{0.425} \times BH^{0.725} \times 0.007184$).

In the formula, BW is the weight (kg), BH is the height (cm), BSA is the body surface area ($m^2$), and SLV is the standard liver volume (ml).

The whole-volume of liver determined by CT liver volumetry was 1038 mL (analyzed by GEHC software, Volume Viewer 9.6.25b; Ge advantage Workstation, General Electric Medical), and the residual liver volume (RLV) was 387 mL, accounting for 38.3% of SLV. As the future liver remnant (FLR) of a liver cirrhosis patient must reach more than 40%, she was prepared to take ALPPS.

Figure 2:
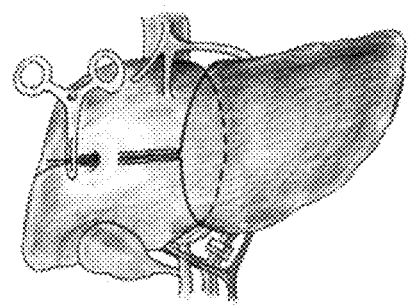
FIG. 2 is a schematic figure of Completely laparoscopic ALPPS using round-the-liver ligation to replace parenchymal transection.

2. Operation Method 2. 1 The first operation:

The patient underwent the first complete laparoscopic operation under general anesthesia on May 14, 2014. The intersection of the left costal margin and the left clavicular line was served as the main manipulation port. Firstly, separated intraperitoneal adhesion with ultrasonic dissector, and then took two accessory ports at the right abdomen. Due to obvious adhesion in the peritoneal cavity, separated intraperitoneal adhesion and the adhesion at the hepatic hilus and the second porta hepatis, dissected the proper hepatic artery, the left hepatic artery and the left portal vein(FIG. 2a), the root of the left portal vein was ligated with silk thread and then occluded with a Hamlock. The left hepatic artery was marked with Proline. Then the treatment of the first porta hepatis was completed. Next, cut off the coronary ligament and the left triangular ligament, and carefully separated the left hemiliver. Dissected the left hepatic vein at the second porta hepatis(FIG. 2b). Pass a wire-assisted nasogastric tube through the right side of the left hepatic vein. Attach the nasogastric tube tightly to the surface of the liver, and move it around to the front of the left caudate lobe. After the left hepatic artery, move the tube around to the front of the liver, near the root of the left hepatic pedicle. Then, put the two ends of the round-the-liver tube together, pull them out of the body through a port in the abdominal wall positioned at the right clavicular line. In addition, the wire-assisted nasogastric tube was put in a 36F chest tube (as outer sleeve for pressing).Tightened the round-the-liver tourniquet and clamped it by a hemal forceps after pushing it into the outer sleeve. Intraoperative ultrasonography was used to determine the diseased part of the liver before tightening the round-the-liver tourniquet (at the left side of the round-the-liver tourniquet, see FIG. 2c). A drainage tube was put into the peritoneal cavity at the hepatic hilus. Then close the peritoneal cavity. The abdominal incision picture after the first operation was seen in FIG. 2d.

Figure 3:
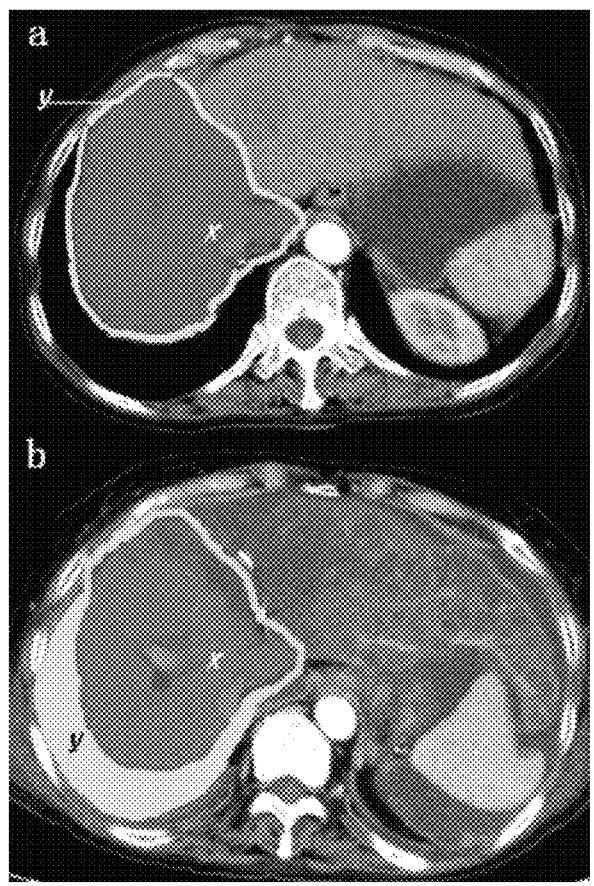
FIG. 3 illustrates the computed tomography before (a) and after (b) our ALPPS (Cai's ALPPS). X represents the inherent right liver, and Y represents the proliferation of right liver.
Figure 4:
FIG. 4 illustrates intraoperative pictures of the first operation in example 1.
Figure 5:
FIG. 5 illustrates intraoperative pictures of the second operation in example 1.
Figure 6:
FIG. 6 illustrates the postoperative liver specimen of ALPPS, which indicates the liver with cirrhosis.
Figure 7:
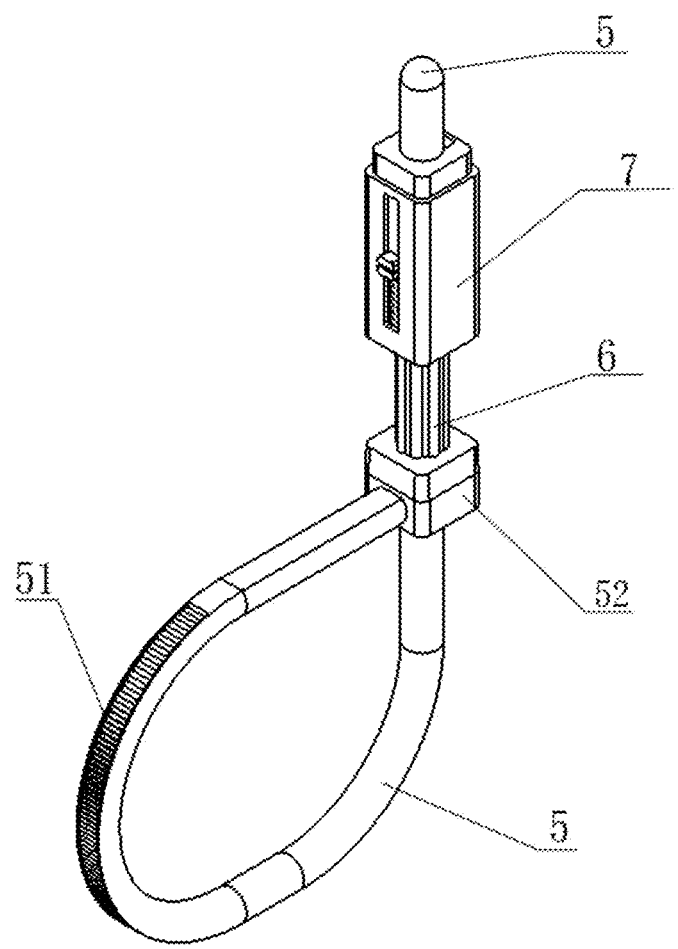
FIG. 7 is a schematic diagram of the working principle of an embodiment of the present invention.
Figures 8A, 8B:
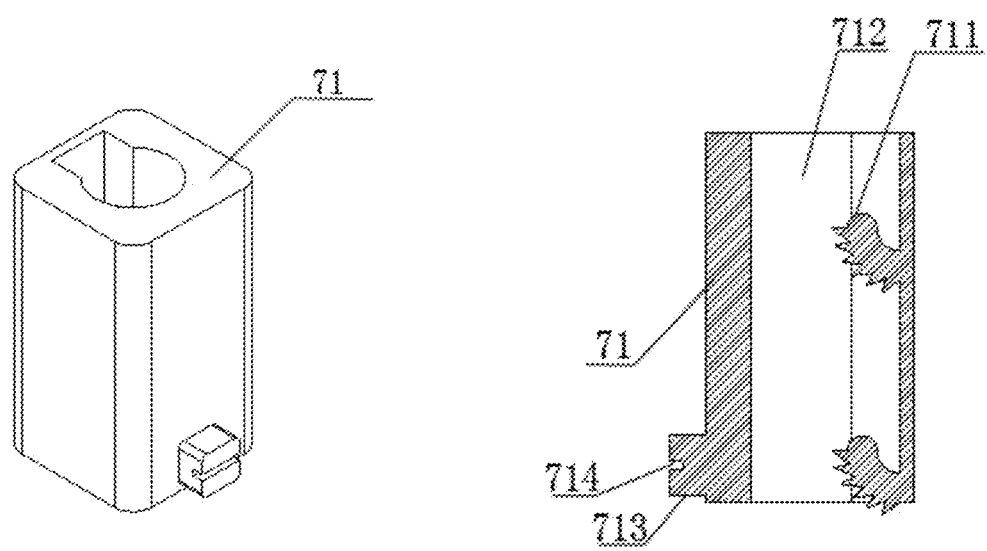
FIG. 8a is a schematic diagram of a buckle according to an embodiment of the present invention
FIG. 8b is a longitudinal cross-sectional view of a buckle according to an embodiment of the present invention.
Figure 9:
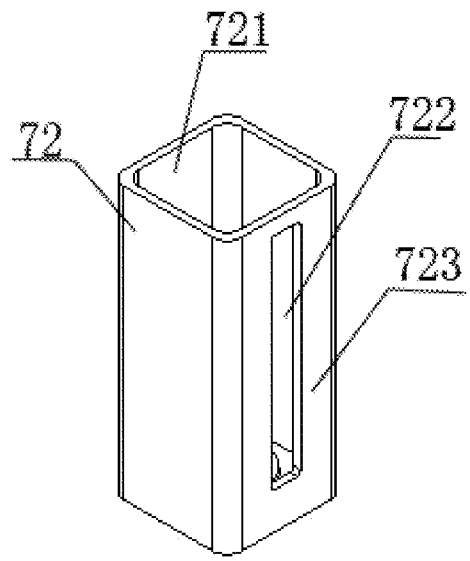
FIG. 9 is a schematic diagram of a first sleeve according to an embodiment of the present invention.
Figure 10:
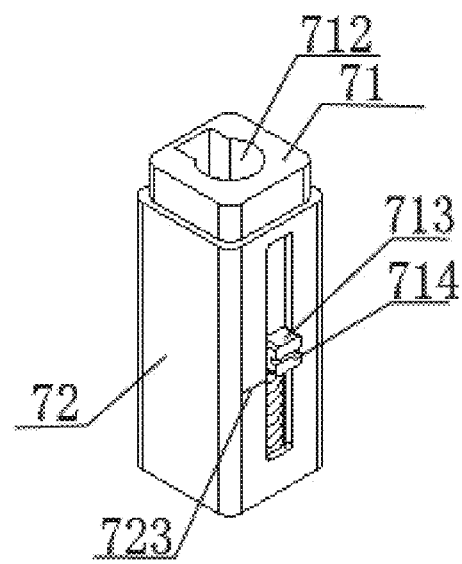
FIG. 10 is a schematic diagram of a pressure control device according to an embodiment of the present invention.
Figure 11:
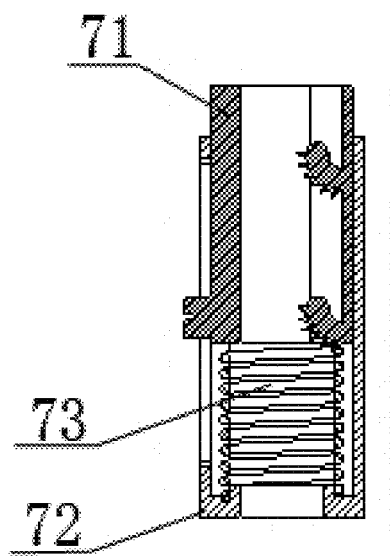
FIG. 11 is a longitudinal sectional view of a pressure control device according to an embodiment of the present invention.
Figure 12:
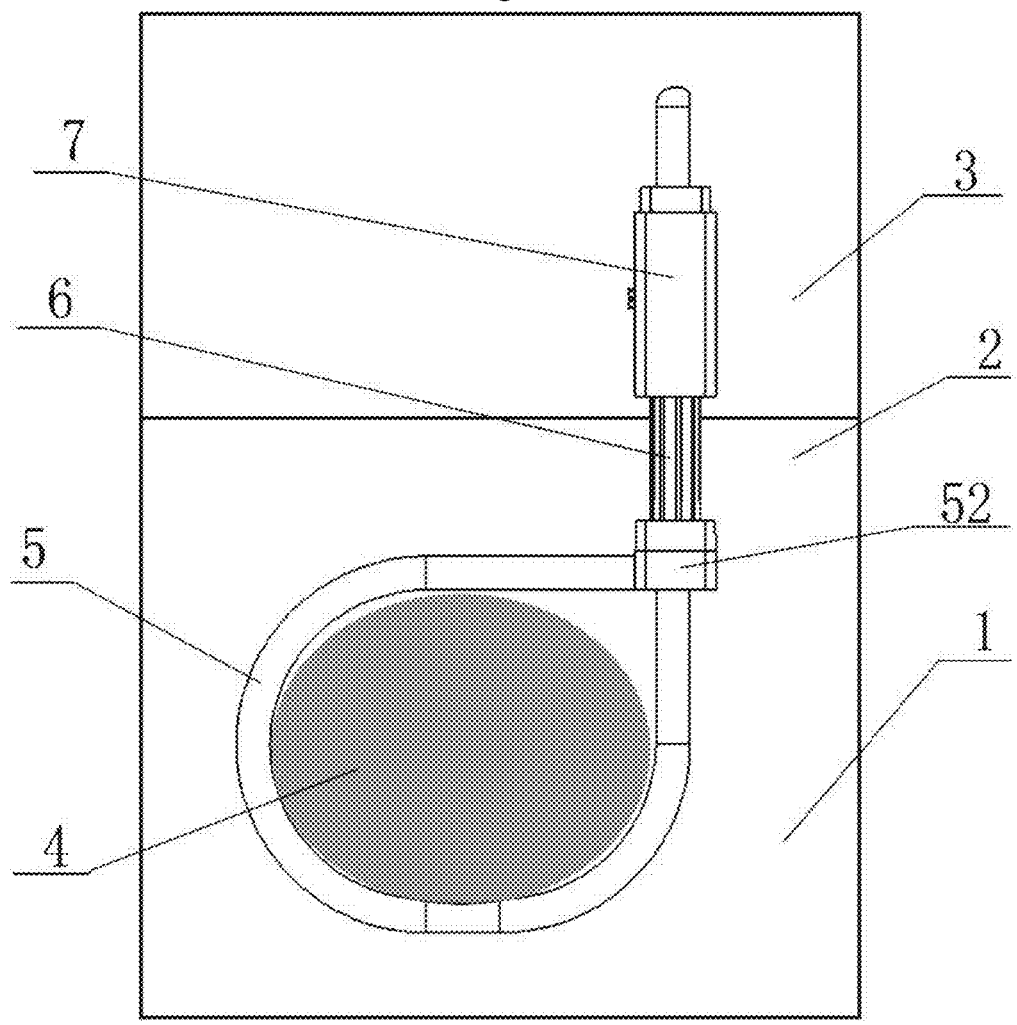
FIG. 12 is a schematic diagram of a use state of an embodiment of the present invention.

2.2 The second staged operation: a laparoscopic left hemihepatectomy was performed on the 11th day after the first operation (i.e. May 25th). Specifically, the operation was performed as follows: firstly, entered the peritoneum through the same port of the first laparoscopic operation. Little loose adhesion, multiple ulcers on the surface of the left liver, which was tightly held against the round-the-liver tourniquet (FIG. 3a) and moderate amount of pale bloody ascites could be observed in the peritoneal cavity. An aspirator was used for cleaning the effusion, also pushing and plucking the adhesions to expose the hepatic portal. Then, assistant lifted the round-the-liver tourniquet through the abdominal wall. The marked left hepatic artery was found at the hepatic portal (FIG. 3b).Then it was occluded and cut off. Later laparoscopic Peng's multifunctional operative dissector (LPMOD) was used to transect the liver parenchyma by curettage and aspiration around the round-the-liver tourniquet (FIG. 3c), which was assisted with an Endo-GIA stapler. The liver parenchyma was transected after confirming that the left hepatic vein had been clipped. And the diseased hemiliver was removed. Properly check for bleeding sites in the peritoneal cavity. A peritoneal drainage tube was retained on the surface of the transection of liver parenchyma, and then the peritoneal cavity was closed (FIG. 3d). Because the volume of the left liver specimen was too large, about 21cm×16 cm, the left liver specimen could not be took out through the port. The specimen was took out through a small incision which was made below the right costal margin (FIG. 4). The operation went smoothly.

3 Result 3. 1 In the first operation, operative time was 290 min, the amount of bleeding was 100 ml, and there was no blood transfusion during the operation. After the first operation, the body temperature of the patient was 36.2-37.7° C., the heart rate was 81-104 times per minute, and the abdominal cavity drainage liquid was 200-1033 ml per day. The patient got up on the 1st postoperative day, and was subjected to B-scan ultra-sonography on the 4th postoperative day, which showed pleural effusion, so catheter drainage was used and the amount of the drainagewas 350~911 ml per day. After the operation, the patient gradually recovered diet. On the 6th day after the first operation, the round-the-liver tourniquet was tightened downward once more. The elastic ring was also moved and it continued to work. On the 2nd postoperative day, ALT reached its peak value—2998 U/L; on the 1st postoperative day, AST reached its peak value— 2232 U/L; the total bilirubin gradually rise after operation, reached its peak value—112.7 μmol/Lon the 4thpostoperative day, and then gradually fell back; the white blood cells and the c reaction proteins reached the peak values on the 2nd and 4th postoperative day respectively; and PT was maintained within the range of 13.9 s to 25.0 s; and APTT was maintained at 36.1 s-44.6 s. The CT examination on the patient was carried out on the 5th postoperative day. The volume of the remaining liver was measured to be 669 mL, increased by 72.9% compared with that before the operation. The CT (computed tomography) was carried out again on the 9th postoperative day, the volume of the residual liver was 753.7 ml, increased by 94.8% compared with that before the operation. The volume of the remaining liver accounted for 74.6% of the volume of the standard liver, namely the expected future liver remnant volume was 74.6% of the volume of the standard liver (FIG. 1).When the liver function returned to normal, there was no infection existed in the abdominal cavity and the nutrition condition was good, the required standard for safe hepatectomy was achieved.

3.2 In the second staged operation, operative time was 160 min, the amount of bleeding was 100 ml, and 2U concentrated erythrocyte was transfused during the operation. The patient got up and resume diet on the 1st postoperative day. The body temperature of the patient was 35.8~37.6° C.; The heart rate was 72-86 times per minute; And blood pressure was stable. The white blood cell mildly rise then gradually reduced, and ALT and AST continuously reduced, and the total bilirubin transiently increase then continuously reduced on the first postoperative day. The abdominal cavity drainage liquid was 300-1100 ml per day and gradually reduced to 24-64 ml.

3. 3 Postoperative histopathological finding revealed that (left liver) hepatocellular carcinoma, coagulative necrosis accompanying with hemorrhage, (hepatic duodenal ligament)no lymph gland cancer metastasis was found (0/2).

Traditionally, methods to promote future residual liver volume increase includes:

(1) Makuuchi's portal vein embolization method (1990).(2)Adam's (2000) second-stage liver resection operation.(3) Jaeck's (2004) second-stage liver resection used for treating multiple left or right half-liver tumors. (4) Clavien's second-stage liver resection operation (2007), in which, all the tumors of the left half-liver is removed in the first-stage operation using joint wedge resection, followed by expanded right half-hepatic resection operation in the second stage after several weeks and the volume of the left half-hepatic is enough. The biggest drawback of these operations is that the interval time between the two operations is too long. It needs on average more than four weeks or even four months. The tumor can continue to progress during this period, and the first operation often leads to the adhesion, so that the second resection operation is more difficult. In addition, the hyperplasia of remaining liver after the operation is not ideal. Compared with the traditional proliferation(10%~46%) in 2~8 weeks, the APPLS's operation features in rapid volume growth of the remaining liver in the 7d (74%~87%); and a second-period operation can be carried out after almost one week. However, postoperative complication rate of the ALPPS is up to 74%. In addition, case fatality rate is reported to be 12%~23%.The operation risk is relatively larger. The occurrence rate of the severe infection is as high as 20%~25%. Which is an important reason for causing high death rate. The liver parenchyma is separated in the first stage, in order to block the communicating blood supply from the portal vein between the two sides, so that the rapid and remarkable proliferation of the remaining liver can be promoted. However, it may cause serious consequences such as bile leakage. Is there any other methods to block the blood communication between the two sides without transection of the liver, so that the rapid liver volume growth can still happen? Depend on previous experience of large amount of round-the-liver lifting and pulling method in various liver resection procedures, we proposed that the liver parenchyma dividing in the ALPPS could be replaced by taking a band around the liver as a tourniquet. Therefore, the liver transection and bile leakage can be prevented. After looking up the literature, we found that Campos also had a similar idea and one operation was carried out in 2011 and 2013 respectively, but all under laparotomy.

There are domestic reports of laparoscopic assisted associating liver partition and portal vein ligation for staged hepatectomy showing optimistic results. However, the reports of ALPPS by a complete laparoscope is hardly seen in the world. There is only two complete laparoscopic liver resection and experience of using round-the-liver lifting and pulling method, so we have achieved good results by combining them The round-the-liver tourniquet not only blocks blood flow between the left and right hemiliver, but also facilitates the operation of transecting liver parenchyma in the second stage. We are accustomed to using the laparoscopic multifunctional operative dissector(LPMOD).When transecting liver parenchyma, the electric coagulation can be enhanced directly on the round-the-liver tourniquet. Moreover, due to the insulation effect of the round-the-liver tourniquet, we do not need to worry about injuring deep tissue, especially the post-hepatic inferior vena cava, so that the liver resection process is safe and reliable.

The arrangement of the round-the-liver tourniquet in the present invention is different from that of traditional methods. Generally, the round-the-liver tourniquet passes through the retrohepatictunnel between the right hepatic vein and the middle hepatic vein. In order to leave the middle hepatic vein to the reserved hemiliver when transecting liver in the second stage, by which the liver function can be better protected. The round-the-liver tourniquet has to pass through the retrohepatictunnel between the left hepatic vein and the middle hepatic vein. Therefore, more attention is required when dissecting at the superior border of the liver.

With respect to the mechanism of rapid proliferation of residual liver after ALPPS, four possible mechanisms are proposed. The application result of the round-the-liver tourniquet indicates that, blocking blood flow communication between the left and right hemilivers, and making all of the blood of the contralateral portal vein flows into the remaining liver serve as the most important factor. The treatment effect of the invention also shows that the ALPPS can also play a role in primary liver cancer accompanied with liver cirrhosis. Because the first-stage operation does not need to divide the liver parenchyma, the liver-wound surface does not exist, so that serious bile leakage complications and infection caused by serious bile leakage complications can be avoided.

In this case, when the tourniquet is lifted up and tightened, the hepatic artery stayed away. However, the left hepatic pedicle is pressed, and the jaundice increased after the operation. This may promote rapid proliferation of the remaining liver, but may also cause adverse effects to the liver function. Therefore, to weigh gains and losses, it is advisable to keep away from hepatic pedicle. In implementation, we well dissected the porta hepatis, so that the tourniquet can penetrate out between the hepatic plate and the liver surface. Therefore, the hepatic pedicle is spared.

With regard to the indication, it is really hard to assess which operation is better: the tumor is small but close to the sagittal section of the portal vein, and the risk of ablation is pretty high, so it is possible that the tumor is not completely ablated; on the one hand, since the liver function grade is Child-A, it is possible to perform hepatectomy for the patient. Nevertheless, the results of CT scan and MR scan of the patient before the operation suggests liver cirrhosis, and the remaining liver volume is only 38%, which is lower than the lower limit of 40%. As a result, there is risk for left hepatectomy. According to this consideration, the two-staged hepatectomy is choosen. The patient can get off the bed the 1st day after the first and the second surgery, suggesting that he recovered well. So the method we chosen can bring benefits to the patient.

In conclusion, through clinical practice, it is considered that the ALPPS two-stage operation can be safely implemented under the laparoscope. Although patients suffer from the primary liver cancer accompanied with liver cirrhosis, ALPPS can also promote the residual liver volume to increase within a short period. Round-the-liver ligation cause less operation injury than liver dissection although round-the-liver ligation is more difficult to operate, which provide second operation opportunity for patients in a short period. Besides, it did not cut the liver parenchyma; some complications such as bile leakage were avoided. Compared to liver dissection, the effect of ALPPS is similar and the complications are obviously less. This means round-the-liver ligation can replace liver dissection; the mechanism of rapid growth of the remnant liver after ALPPS is that all the blood of the portal vein of the opposite side flows into the remnant liver caused by the block of traffic of blood flow from the left side and the right side.

In this case, completely laparoscopic ALPPS by using round-the-liver ligation instead of liver parenchyma dissection has good results, and the growth of the remnant liver is rapid in a short period. Considering this is only a preliminary practice, we need more cases to prove the effect and study the mechanism deeper with animal experiments.

EXAMPLE 2

The patient received liver ablation for liver cancer in a hospital in Beijing 2 years ago. No obvious discomfort is complained after the operation, and AFP is in normal level during follow up every three months. Two months ago, the patient get a TACE. From then to now, the patient complains discomfort of the right upper quadrant. However, there is no other obvious abnormity. Now for further treatment, the patient is admitted into our hospital for "liver cancer, after TACE". The patient has the chronic hepatitis B for 16 years and is treated with Adefovir tablet in dosage of 1 tablet qd.

Before operation, the CT scan result shows the remanent liver volume accounts for 35.6% of the standard liver volume. The futural remanent liver volume of the liver cirrhosis patient is required to reach more than 40%, so the right half liver is about to be dissected by the method of two-steps hepatectomy using laparoscopic round-the liver ligation.

Operation of the first-stage surgery was carried out at May 22, 2014. No obvious metastatic knot and no ascites was found in abdominal cavity during the operation. The liver is nodular, the liver is easy to bleed after touched, the left liver volume is normal, the right liver is thick, a mass with a diameter of 5 cm is found in the right liver inner VIII section and a mass with a diameter of 0.8 cm is found in the right liver VI section. The size of the gallbladder is about 7*3 cm with stones formed inside.

In the First-stage operation, the patient was placed in the supine position under general anesthesia, with routine catheterization. An small incision was formed 5 cm away from the right side of the navel, the pneumoperitoneum needle was used for puncturing the abdominal cavity, and the carbon dioxide gas was set at 15 mmHg. Then the laparoscope was inserted through the cavity, we can have a view of the abdominal cavity. A 12-mm trocar below the right costal margin was inserted as the manipulation port. Two 5-mm trocars were inserted as assistant manipulation ports at the right anterior axillary line and the midaxillary line. An ultrasonic knife was first used for separating adhesion in the abdominal cavity .The right liver was freed sufficiently and pulled to the left side, the short blood vessels were separated and ligation, the second porta hepatis was dissected, and the right hepatic vein were separated. Next, we began to separate the hepatic duodenal ligament. The gallbladder was cut off due to the gallstone.The left hepatic artery and the right hepatic artery ware freed, and then the right branch of portal vein and the hepatic caudal lobe were separated. The right branch of portal vein was lighted and clipped with a Hamlock. We used a jejunum nutrition tube with a guide core. The tube was passed between the right hepatic vein and the liver surface and was further passed between the right hepatic artery and liver surface. The tube was wrapped around the liver along the future transection line and was closed by the manner that is used in Pringle's maneuver. Both ends of the tube were passed through a 36F thorax tube with a length of about 10 cm. It was passed through the abdominal wall through a small incision, and the tube was locked with a forceps outside the abdominal cavity .The forceps was wrapped around with rubber to increase friction. At last, the abdominal cavity was washed again, and the abdominal drainage tube was placed in the hepatic portal. And we finished the first stage. Surgery went smoothly, with blood loss volume at 100 ml. Patient vital sign is stable. The anesthesia level is satisfied. Then the patient is sent to PACU.

The patient was allowed off-bed activity at the first day after the first-step operation. The glutamic pyruvic transaminase (ALT) and the glutamic acid transaminase (AST) reached the peak at 1520 U/L and 1460 U/L respectively. The round-the-liver ligature was tightened once on 6 days after the first-step operation. The future liver remnant volume was 670 ml,which was increased 37.9% according to the CT scan on Day 10 after the first-stage operation. After the CT reconstruction, we measured the future liver remnant volume was 49.1% of the standard liver volume. The second-stage operation that right hemihepatectomy was performed on Day 14 after the first-stage operation.

In the second-stage operation, no obvious metastasis knot exist in the abdominal cavity. There was a little ascites. The liver is nodular. Left half-liver volume was increased, and there was no obvious abscess on the surface of the liver. We could see the round-liver-ligation was in situ, and the right hepatic artery ligature was in position. The right hemihepatectomy was then performed , and a 1.5 cmtumer was seen under the liver VIII section, the cut surface of the tumer was grey-white. The remaining organs remain abnormal.

In the second-stage operation, the patient was placed in the supine position under general anesthesia, with routine catheterization, the pneumoperitoneum needle was used for puncturing the abdominal cavity as the same as the first-stage operation, and the carbon dioxide gas was set at 15 mmHg. And the laparoscope was inserted through the cavity. A 12-mm trocar below the left costal margin was inserted as the manipulation port. Two 5-mm trocars were inserted as assistant manipulation ports at the right anterior axillary line. The aspirator was used for separate adhesion in the abdominal cavity. We separated, clipped and then cut off the right hepatic artery. And then the right hemihepatectomy was performed using the laparoscopic multifunctional operative dissector (LPMOD),the round-liver ligation was pull outer the abdominal wall at the same time. Due to the fact that the liver parenchyma was substantially rare after being bound and there were more vascular structures in position. The EC/60 was recommend to use. The right liver was huge in size and could not be taken out from the original incision; we took the specimen from a new incision below the xiphoid. After taking out the specimen, we performed cholangiography. The left liver bile duct and the right liver bile duct could be seen clearly. There was no obvious bile leakage. In the end, the abdominal cavity was washed again, and two abdominal drainage tubes were placed in the hepatic portal. During the second-stage operation, the bleeding volume was about 300 ml. During the surgery, the patient vital sign is stable. The anesthesia is satisfied and patient was sent to PACU for further recovery.

The patient recovers well after the operation and get off the bed in the first day after the operation. The pathological diagnosis: liver cancer.

EXAMPLE 3

This embodiment introduces a special instrument for implementing the completely laparoscopic staged hepatectomy using round-the-liver ligation. It is a pressure-adjustable liver tightening device.

The reference signs in FIGS. 8a-13 are: abdominal cavity 1, abdominal wall 2, external of body 3, liver 4, liver-around band 5 (including first ratchet 51, base 52), abdominal wall catheter 6, pressure control device 7 which includes a buckle 71, a first sleeve 72, and a spring 73; the buckle 71 includes a second ratchet tooth 711, a second inner hole 712, a protruding portion 713, and a vernier 714; the first sleeve 72 includes a first inner hole 721, a guide groove 722, a scale 723.

A special instrument for implementing the completely laparoscopic staged hepatectomy using round-the-liver ligation, a pressure-adjustable liver tightening device, including a liver-around band 5 made of flexible materials of which One end is a free end, and the other end is provided with a through hole. The free end passes through the through hole to form a loop that can tighten the liver 4; the side of the liver-around band 5 facing away from the liver is defined as the outside; The outer side of the liver-around band 5 is provided with first ratchet teeth 51; the free end of the liver-around band 5 passes through the through hole, the abdominal wall catheter 6, and the pressure control device 7 in sequence, and the abdominal wall catheter 6 passes through the patient's abdominal wall 2.

The pressure control device 7 includes a first sleeve 72 and a buckle 71. The direction of the central axis of the first sleeve 72 is taken as the longitudinal direction. The first sleeve 72 is provided with a longitudinal first inner hole 721 for passing through the liver-around band 5, and the buckle 71 is fixed in the longitudinal guide groove 722 of the first sleeve 72 and can move longitudinally along the guide groove 722; the buckle 71 is provided with a second ratchet tooth 711 extending into the first inner hole 721; When the liver-around band 5 passing through the first sleeve 72, the first ratchet tooth 51 meshes with the second ratchet tooth 711; the second ratchet tooth 711 allows the first ratchet tooth 51 to slide in the positive direction of tightening the loop while preventing the first ratchet tooth 51 from sliding in the reverse direction.

A spring 73 arranged in the longitudinal direction is installed between the buckle 71 and the first sleeve 72.

The buckle 71 is provided with a vernier 714 for marking the tightness of the liver-around band 5, and a scale 723 of the vernier 714 is provided on the first sleeve 72.

Preferably, the buckle 71 is a second sleeve sleeved in the first sleeve 72 which is provided with a longitudinal second inner hole 712 for passing the liver-around band 5; The outer wall of the second sleeve is provided with a protruding portion 713 which is slidably inserted in the longitudinal guide groove 722 on the first sleeve 72, and the aforementioned vernier 714 is provided on the protruding portion 713, and the inner wall of the second sleeve is provided with the second ratchet tooth 711.

The other end of the liver-around band 5 opposite to the free end is provided with a base 52, and the through hole is provided on the base 52; under the pulling force of the liver-around band 5, the first sleeve 72 and the abdominal wall catheter 6 and the base 52 press in sequence to position the liver-around band 5.

In this embodiment, in the first stage of the operation, the liver-around band 5 is tightened on the connecting part of the left and right liver lobes. The doctor pulls the liver-around band 5 upwards on the upper part of the first sleeve 72 outside the patient's body. When the vernier 714 is aligned with the preset scale 723 on the first sleeve 72, stop pulling the liver-around band 5, and the first ratchet tooth 51 engages with the second ratchet tooth 711, and the liver-around band 5 is positioned. At this time, the tightening force of the liver-around band 5 on the liver automatically reaches the preset value. Therefore, the tightening force of the liver-around band 5 on the liver can be determined according to the design of the surgical instrument in advance, and it is no longer dependent on the personal feel and experience of the surgeon.

In this embodiment, when the liver-around band needs to be tightened downward on the 6th day after the operation of the first stages, there is no need to open the abdomen, as long as the upper part of the first sleeve 72 outside the body is twitched upwards, when the vernier 714 is aligned with the scale 723 of the first sleeve 72, and the surgeon can fix the position of the liver-around band 5, thus the rely on the personal experience of the physician can be avoided. It is convenient and quick, convenient for doctors to operate, and reduces the pain of the patient.

What is claimed is:

1. A instrument for implementing the completely laparoscopic staged hepatectomy comprising a liver-around band made of flexible materials of which one end is a free end, and the other end is provided with a through hole; the free end passes through the through hole to form a loop that can tighten the liver; the side of the liver-around band facing away from the liver is defined as the outside; wherein, an outer side of the liver-around band is provided with first ratchet teeth; the free end of the liver-around band passes through the through hole, an abdominal wall catheter, and a pressure control device in sequence, and the abdominal wall catheter passes through the patient's abdominal wall;

the pressure control device includes a first sleeve and a buckle, the direction of the central axis of the first sleeve is taken as the longitudinal direction, the first sleeve is provided with a longitudinal first inner hole for passing through the liver -around band, and the buckle is fixed in the longitudinal guide groove of the first sleeve and can move longitudinally along the guide groove; the buckle is provided with a second ratchet tooth extending into the first inner hole; when the liver-around band passing through the first sleeve, the first ratchet tooth meshes with the second ratchet tooth; the second ratchet tooth allows the first ratchet tooth to slide in the positive direction of tightening the loop while preventing the first ratchet tooth from sliding in the reverse direction;

a spring arranged in the longitudinal direction is installed between the buckle and the first sleeve;

the buckle is provided with a vernier for marking the tightness of the liver-around band, and a scale of the vernier is provided on the first sleeve.

2. The instrument according to claim 1, which is characterized in wherein the buckle is a second sleeve sleeved in the first sleeve which is provided with a longitudinal second inner hole for passing the liver-around band; the outer wall of the second sleeve is provided with a protruding portion which is slidably inserted in the longitudinal guide groove on the first sleeve, and the aforementioned vernier is provided on the protruding portion, and the inner wall of the second sleeve is provided with the second ratchet tooth.

3. The completely laparoscopic staged hepatectomy according to claim 1, wherein the other end of the liver-around band opposite to the free end is provided with a base, and the through hole is provided on the base; under a pulling force of the liver-around band, the first sleeve and the abdominal wall catheter and the base press in sequence to position the liver-around band.

\* \* \* \* \*